US012773569B2

(12) United States Patent
Vieau

(10) Patent No.: US 12,773,569 B2
(45) Date of Patent: Oct. 27, 2026

(54) SYSTEMS AND METHODS FOR THE TREATMENT OF CONGESTION

(71) Applicant: MUCEX, INC., North Miami Beach, FL (US)

(72) Inventor: David Pierre Vieau, North Miami Beach, FL (US)

(73) Assignee: MUCEX, INC., North Miami Beach, FL (US)

( * ) Notice: Subject to any disclaimer, the term of this patent is extended or adjusted under 35 U.S.C. 154(b) by 0 days.

(21) Appl. No.: 18/977,486

(22) Filed: Dec. 11, 2024

(65) Prior Publication Data

US 2025/0186795 A1 Jun. 12, 2025

Related U.S. Application Data

(60) Provisional application No. 63/731,251, filed on Apr. 16, 2024, provisional application No. 63/629,895, filed on Dec. 11, 2023.

(51) Int. Cl.

| | |
|---|---|
| ***A61N 1/40*** | (2006.01) |
| ***A61N 1/08*** | (2006.01) |
| ***A61N 7/02*** | (2006.01) |

(52) U.S. Cl.
CPC ............... *A61N 1/403* (2013.01); *A61N 1/08* (2013.01); *A61N 7/02* (2013.01)

(58) Field of Classification Search
CPC ............. A61N 1/403; A61N 1/08; A61N 7/02
See application file for complete search history.

(56) References Cited

U.S. PATENT DOCUMENTS

| | | | | |
|---|---|---|---|---|
| 6,058,932 | A * | 5/2000 | Hughes | A61M 16/0006 482/13 |
| 8,181,656 | B2 * | 5/2012 | Danek | A61B 17/24 607/42 |
| 11,304,746 | B2 | 4/2022 | Wolf et al. | |
| 2007/0027431 | A1 * | 2/2007 | Korb | A61B 17/22004 604/289 |
| 2007/0141106 | A1 | 6/2007 | Bonutti et al. | |
| 2008/0195001 | A1 | 8/2008 | Werner | |
| 2011/0178441 | A1 | 7/2011 | Tyler | |

(Continued)

FOREIGN PATENT DOCUMENTS

| | | | |
|---|---|---|---|
| IN | 202411083560 | A | 11/2024 |
| WO | 2015/106118 | A1 | 7/2015 |

(Continued)

OTHER PUBLICATIONS

International Search Report and Written Opinion for PCT/US2024/059663 dated Mar. 24, 2025. (17 pages).
Heggannavar e al.; "A Randomised Controlled Study to Evaluate the Effectiveness of Shortwave Diathermy in Acute Sinusitis"; International Journal of Physiotherapy and Research, Int J Physiother Res 2017, vol. 5(3):2066-2072.

(Continued)

*Primary Examiner* — Sean A Frith
(74) *Attorney, Agent, or Firm* — ROTHWELL, FIGG, ERNST & MANBECK, P.C.

(57) ABSTRACT

The present disclosure relates to methods and devices for reducing congestion of the respiratory system by applying diathermy, including radiofrequency (RF) energy, and ultrasound energy, to increase the temperature of mucus. This controlled heating reduces mucus viscosity and elasticity, facilitating mucus clearance and improving respiratory function. Embodiments of a device including a wand, a mask, and a vest are also described herein.

15 Claims, 10 Drawing Sheets

(56) References Cited

U.S. PATENT DOCUMENTS

| | | | | |
|---|---|---|---|---|
| 2012/0179073 | A1 | 7/2012 | Nita | |
| 2014/0148735 | A1 | 5/2014 | Nau, Jr. | |
| 2014/0257262 | A1 | 9/2014 | Carpentier et al. | |
| 2015/0320481 | A1* | 11/2015 | Cosman, Jr. | A61B 18/1233 606/35 |
| 2016/0151646 | A1* | 6/2016 | Bonutti | A61N 7/00 601/2 |
| 2016/0278845 | A1* | 9/2016 | Mayse | A61B 18/1815 |
| 2017/0014258 | A1 | 1/2017 | Wolf et al. | |
| 2019/0290314 | A1* | 9/2019 | Gemer | A61M 25/0113 |
| 2019/0343581 | A1* | 11/2019 | Panescu | A61B 18/1492 |
| 2021/0228914 | A1* | 7/2021 | Barthe | A61B 8/4281 |
| 2022/0032090 | A1 | 2/2022 | Gonzalez Joven | |
| 2022/0233209 | A1* | 7/2022 | Borody | A61B 1/015 |
| 2024/0261172 | A1 | 8/2024 | Plager et al. | |
| 2024/0299235 | A1 | 9/2024 | Hansen et al. | |
| 2024/0316299 | A1 | 9/2024 | Mithalal | |
| 2024/0366286 | A1 | 11/2024 | Wolf et al. | |

FOREIGN PATENT DOCUMENTS

| | | | |
|---|---|---|---|
| WO | 2018/008020 | A1 | 1/2018 |
| WO | 2020/226629 | A1 | 11/2020 |
| WO | 2021/022320 | A1 | 2/2021 |

OTHER PUBLICATIONS

W. P. E. Paterson; "The Treatment of Nasal Sinus Infection by Ultra-Short Wave Diathermy"; The Canadian Medical Association Journal; May 1940; vol. 42(5); pp. 454-456.

S.H.M. Blackwood, et al.; "Shortwave Diathermy (S.W.D.) in the Treatment of Unresolved Pneumonia"; Sep. 1980, 2 pages.

Diathermy in Independence at Back & Neck Pain Center; Back & Neck Pain Center; Wayback Machine; Aug. 2021; https://www.dotybackandneckpain.com/diathermy; 1 page.

R. S. Khandpur; "Short-Wave Diathermy Machine"; (2019); https://www.researchgate.net/publication/337931739_Short-Wave_Diathermy_Machine. (5 pages).

* cited by examiner

SYSTEMS AND METHODS FOR THE TREATMENT OF CONGESTION

CROSS REFERENCE TO RELATED APPLICATIONS

This application claims priority to U.S. Provisional Patent Application Nos. 63/629,895, filed on Dec. 11, 2023, and 63/731,251, filed on Apr. 16, 2024, each of which are incorporated by reference herein in their entirety.

FIELD OF THE INVENTION

The subject matter disclosed herein generally relates to medical equipment, specifically diathermy instrumentation and high-frequency vibration devices, customized apparatus designed to direct heat and energy delivery to an affected area in the human body while avoiding damage to associated tissue.

BACKGROUND OF THE INVENTION

When an individual experiences the common cold, flu, or other respiratory illness, they often suffer from congestion which builds up in the respiratory system, including lungs, nasal passages, sinus cavities and in the middle ear cavity. The passages between the source of the fluids in the nasal cavity and the ear and throat are designed to drain the fluids into the digestive tract where they are processed.

However, a thickening of the fluid often naturally occurs during the healing process causing "heavy" (or "thick") mucus, sputum, or phlegm, to become trapped in the passages, lungs, sinus cavities, and/or middle ear creating a blockage. This blockage makes it difficult for fluid to drain properly and the fluid buildup creates pressure and an elevated degree of discomfort for the individual. Bacteria may build up in the heavy mucus creating an infection requiring treatment with antibiotics.

Much effort has been applied to determining ways to eliminate and/or drain these heavy fluids including pharmaceutical medications which are designed to 'thin' heavy fluids or reduce inflammation as well as a large number of physical therapy approaches (including the Valsalva maneuver) to manipulate the affected areas to promote fluid flow. Hot steam introduced into the nasal passages warms the channels, adds moisture, and can promote flow. Hot compresses applied externally to the face/ear provides warmth which will 'thin' the heavy mucus promoting flow and thereby relieving the symptoms. Often, combinations of all of the above are applied in an effort to relieve the discomfort.

The use of hot compresses has limited impact due to the limitation in heat transfer through human tissue so getting the heavy mucus warm enough to 'thin' it and create flow is challenged. Steam also loses temperature quickly as it enters the nasal passages limiting its heating effect on heavy fluids deposited in the sinus cavities and middle ear where the effects are most problematic. The use of medications often does provide temporary relief but often come with unpleasant side effects and in some cases may make the conditions worse over time. Physical therapy approaches may also provide relief and are usually effective if the fluid is only slightly thickened. In some individuals the shape of the passages may further constrain proper flow (in children, for example).

Diathermy, or the use of radiofrequency (RF) energy, has been utilized in the medical field to create controlled heat which targets specific tissue in the body for removal or repair of problematic tissue or symptoms. Applications which have been broadly implemented focus on surgical procedures and on "deep heating" muscles, joints and tissue for therapeutic purposes. It is commonly used for muscle relaxation, and to induce deep heating in tissue for therapeutic purposes.

High-frequency vibration (or ultrasonic energy) devices have also been used in the medical field in diverse applications including rehabilitation, offering potential benefits for pain management, muscle relaxation, circulation, bone health, physical rehabilitation, and lymphatic drainage. However, neither of these approaches has been utilized to affect the temperature, yield stress, viscosity, elasticity, and/or sliding yield stress of the mucus itself as an approach to relieve or treat congestion including in the field of otolaryngology (medical specialty focused on ear, nose, and throat).

There exists an unmet need to target mucus itself. No existing therapies apply diathermy, high-frequency vibration, and/or a combination of both to break chemical bonds located in the "thick" mucus trapped in lungs, sinus and middle ear cavities, and connecting passageways, thinning the fluid to promote flow and relieve symptoms.

SUMMARY OF THE INVENTION

The subject invention targets mucus, including thick mucus, by applying diathermy, high-frequency vibration, and/or a combination of both diathermy and high-frequency vibration to thin the "thick" mucus trapped in the respiratory system, including sinus and middle ear cavities, to promote flow and relieve symptoms.

The subject invention applies diathermy, including RF energy, and/or high-frequency vibration, including ultrasound (or "ultrasonic") energy, to target fluids, including mucus, at energy levels which provide the necessary heat to raise the fluid temperature, break chemical bonds within the fluid, and/or modify the adhesion properties of the mucus sufficiently to "thin" and/or loosen said mucus without creating damaging excess heat in skin and surrounding tissue and organs.

In accordance with one embodiment of the invention, provided herein is a method for treating congestion, the method comprising applying radiofrequency (RF) energy and/or ultrasound energy to a subject having mucus; wherein the RF energy and/or ultrasound energy increases the temperature of the mucus to a range sufficient to reduce its viscosity and elasticity; wherein the temperature is between about 98.0° F. and about 112.0° F.

In some aspects, the RF energy parameters is applied at:

a) a frequency of about 10.0 MHz to about 3 GHZ;

b) a power level of about 1 W to about 300 W; and/or c) a duration of exposure of about 1 to about 60 minutes.

In some aspects, the frequency of the RF energy is about 10 MHz. In some aspects, the power level of the RF energy is about 1 W. In some aspects, the duration of exposure of the RF energy is about 8 minutes.

In some aspects, the ultrasound energy is applied at:

a) a frequency of about 20.0 kHz to about 10.0 MHz;

b) an amplitude of about 0.01 mm to about 1.00 mm; and/or c) a duration of exposure of about 1 to about 60 minutes.

In some aspects, the mucus is thick mucus. In some aspects, the mucus is heavy mucus. In some aspects, the mucus viscosity decreases by about 10 percent to about 50 percent compared to its baseline viscosity. In some aspects, the RF energy and/or ultrasound energy reduces the binding interaction between bound water and mucins, facilitating mucus clearance. In some aspects, the RF energy and/or ultrasound energy breaks chemical bonds which create the elasticity and stickiness of the mucus.

In some aspects, the method further comprises measuring mucus temperature using a temperature sensor; and adjusting the RF energy and/or ultrasound energy to prevent overheating of mucus.

In some aspects, the RF energy and/or ultrasound energy is applied to sinus cavities at a depth of about 1 to about 3 cm below the skin surface.

In some aspects, the method further comprises the step of combining the RF energy and/or ultrasound energy application with external air pressure modulation, such as coughing, forced expiratory maneuver, Huff Coughing, and/or the Valsalva maneuver.

In some aspects, the increase in temperature modifies the mechanical properties of the mucus. In some aspects, the increase in temperature modifies the chemical properties of the mucus.

In another exemplary embodiment of the invention, provided herein is a device for the treatment of congestion, comprising an RF energy and/or ultrasound energy generator configured to operate at a frequency range of about 10.0 MHz to about 3.0 GHz for RF energy and/or about 20.0 kHz to about 10.0 MHz for ultrasound energy; at least one applicator configured to deliver said RF and/or ultrasound energy to mucus at an energy level sufficient to raise the temperature of the mucus to between about 98.0° F. and about 112.0° F.; a control unit configured to a) monitor temperature changes in real-time to ensure safety; and b) modulate the frequency, power level, and duration of energy delivery; and a feedback system to adjust parameters based on user-specific mucus properties.

In some aspects, the device comprises an RF energy generator. In some aspects, the device comprises an ultrasound energy generator. In some aspects, the device comprises an RF energy and ultrasound energy generator.

In some aspects, the applicator is configured for use on the sinus region and includes an ergonomic design to conform to facial contours.

In some aspects, the device further comprises a temperature-controlled mechanism to limit heating to a maximum of about 120.0° F.

In some aspects, RF energy and/or ultrasound energy generator of the device is capable of pulsed delivery to minimize risks associated with continuous heating. In some aspects, the control unit of the device includes pre-programmed treatment protocols based on mucus viscosity.

In some aspects, the device is a wand, mask, or vest. In some aspects, the device comprises more than one applicator. In some aspects, the more than one applicators are employed simultaneously.

The above and other various aspects and embodiments are described below with reference to the accompanying drawings.

BRIEF DESCRIPTION OF THE DRAWINGS

The accompanying drawings, which are incorporated herein and form part of the disclosure, help illustrate various embodiments of the present invention and, together with the description, further serve to describe the invention to enable a person skilled in the pertinent art to make and use the embodiments disclosed herein.

(FIG. 4A) and 108° F. (FIG. 4B). The arrowed line indicates critical pressure.

FIG. 5A shows a front-on view of the device, wherein the device is a wand. FIG. 5B shows an application of the device wherein the device is applied to the face of a patient. FIG. 5C shows an application of the device wherein the device is applied to the back of a patient.

FIG. 6A shows a rear-view of the device, wherein the device is a mask. FIG. 6B shows an application of the device, wherein the device is applicable and attachable to the face of a patient for wearing without the use of hands.

DETAILED DESCRIPTION OF THE INVENTION

Figure 1:
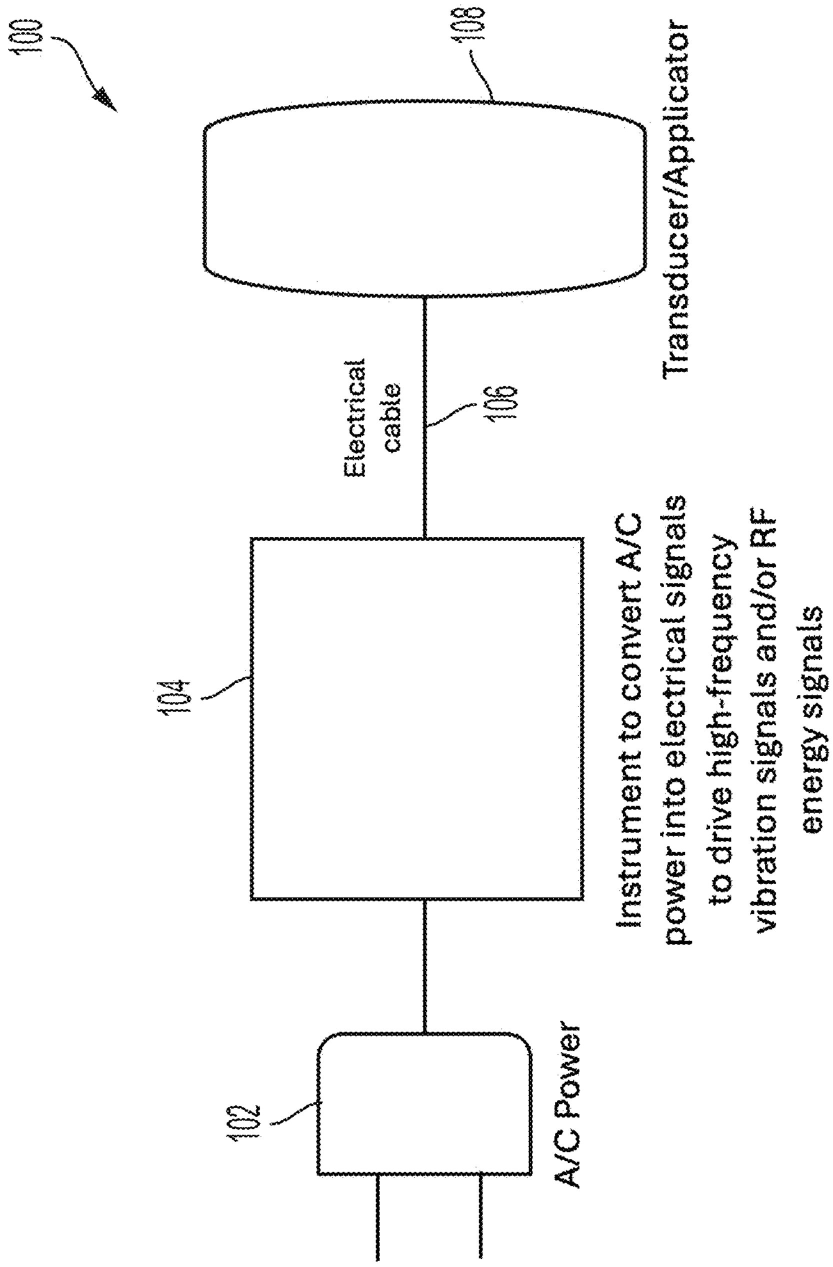
FIG. 1 shows an embodiment of the device.

This invention implements the use of diathermy, including radiofrequency (RF) energy and/or high-frequency vibration, including ultrasound energy (also referred to herein as "ultrasonic" energy) for the treatment of congestion in the respiratory system by penetrating deeply into the affected areas to thin and/or loosen thick or heavy mucus which blocks passages, lungs, middle ear and/or sinus cavities, promoting flow and clearing the obstruction and associated symptoms.

The respiratory system is responsible for gas exchange and includes airways lined with mucosal surfaces that produce mucus to trap and remove inhaled particles, pathogens, and debris. Proper mucus production and clearance are essential for maintenance of airway patency and for preventing respiratory complications, but excessive buildup of mucus, especially thick or heavy mucus, can lead to congestion, impaired breathing, and other health complications.

In some embodiments, the combination of heating (including via RF energy) and vibration (including via ultrasound energy) synergistically causes mucus clearance. In some embodiments, heating (including via RF energy and/or ultrasound energy) provides the primary therapeutic effect. In some embodiments, vibration (including via ultrasound energy) provides the primary therapeutic effect. In some embodiments, heating and vibration provide a combined therapeutic effect.

Diathermy is a therapeutic technique that uses high-frequency electromagnetic currents or ultrasound to generate heat within mucus and/or body tissues. Diathermy may be employed to improve blood flow, reduce pain, and facilitate tissue healing by deep heating muscles, joints, or tissues without burning the skin.

In some embodiments, the diathermy may be radiofrequency (RF) diathermy ("RF energy"). RF energy may be used in medical therapy applications with specific frequency and amplitude ranges tailored to the therapeutic goals, such as tissue heating, ablation, or stimulation. In some embodiments, RF diathermy comprises the application of RF energy delivered to mucus at controlled parameters to ensure safety and efficacy. In some embodiments, RF energy may generate heat through resistive interactions with mucus. In some embodiments, RF energy may generate heat through resistive interactions with tissue. In some embodiments, RF energy may generate heat through resistive interactions with mucus and tissue. In some embodiments, RF energy may effectively increase the temperature of mucus to a therapeutic range in order to decrease mucus viscosity and allow the mucus to flow, reducing congestion.

In some embodiments, RF energy is applied using electromagnetic waves in the range of about 10.0 MHz to about 3.0 GHz. In some embodiments, the RF energy may have a frequency of between about 10 MHz and about 50 MHz, between about 25 MHz and about 250 MHz, between about 50 MHz and about 500 MHz, between about 1 GHz and about 3 MHZ, between about 500 MHz and about 2.5 GHZ, between about 750 MHz and about 1.5 GHz, or between about 1 GHz and about 3 GHz.

For example, in some preferred embodiments, the RF energy may have a frequency of about 13.56 MHz, of about 27.12 MHz, about 40.68 MHz, or about 2.45 GHz, which are widely used in industrial, scientific, and/or medical fields.

In some embodiments, the power level of the RF energy ranges from 1 W to about 300 W. In some embodiments, the power level of the RF energy is about 1 W, about 5 W, about 10 W, about 25 W, about 50 W, about 100 W, about 150 W, about 200 W, about 250 W, or about 300 W. In some embodiments, the power level of the RF energy may be between about 1 W and about 10 W, between about 5 W and about 25 W, between about 20 W and about 80 W, between about 75 W and about 150 W, between about 100 W and about 200 W, or between about 150 W and about 300 W.

In some embodiments, the duration of application or exposure of the RF energy ranges from about 30 seconds to about 60 minutes. In some embodiments, the duration of exposure of RF energy is about 30 seconds. In some embodiments, the duration of exposure of RF energy is about 1 minute. In some embodiments, the duration of exposure of RF energy is about 5 minutes. In some embodiments, the duration of exposure of RF energy is about 8 minutes. In some embodiments, the duration of exposure of RF energy is about 10 minutes. In some embodiments, the duration of exposure of RF energy is about 15 minutes. In some embodiments, the duration of exposure of RF energy is about 30 minutes. In some embodiments, the duration of exposure of RF energy is about 45 minutes. In some embodiments, the duration of exposure of RF energy is about 60 minutes. In some embodiments, the duration of exposure of RF energy is between about 1 minute and about 5 minutes, between about 5 minute and about 15 minutes, between about 10 minutes and about 30 minutes, between about 15 minutes and about 45 minutes, or between about 30 minutes and about 60 minutes.

It is understood that, in some embodiments, the RF energy may comprise microwave diathermy or shortwave diathermy.

Microwave diathermy is a specific type of diathermy which uses electromagnetic waves in the microwave frequency range to produce localized heating in mucus or tissue. The heat is generated by the oscillation of water molecules and ions within the mucus or tissue, which absorb microwave energy. Microwave diathermies typically operate at a range between about 300 MHz and about 3 gGz. Microwave diathermies typically operate at a power level of between about 50 and about 500 W of total power. In some aspects, the power output of microwave diathermy may be pulsed or modulated.

Shortwave diathermy (SWD) is a specific type of diathermy which operates at specific frequencies within the RF range, primarily at about 27.12 MHz. SWD typically operates at about 27.12 MHz, at about 13.56 MHz, or at about 40.68 MHz. SWD typically operates at a power level of between about 80 and about 400 W. In some aspects, the power output of SWD may be pulsed or modulated.

In some embodiments of the present invention, the high-frequency vibration may be ultrasound or ultrasonic energy. The high-frequency vibration, which may operate at frequencies overlapping or distinct from said diathermies, including RF energy, may be further applied to enhance mucus mobilization. In some embodiments, the high-frequency vibration may induce shear forces that mechanically disrupt mucus adhesion and facilitate mucus movement within the respiratory system, including airways.

In some embodiments, high-frequency vibration may comprise the application of ultrasound energy delivered at controlled parameters to ensure safety and efficacy to a subject to treat congestion. Ultrasound waves generate heat through mechanical vibration and absorption by mucus and tissue.

In some embodiments, the high-frequency vibration may be ultrasound energy, and the ultrasound energy may have a frequency of between about 20.0 kHZ (0.02 MHZ) and about 10.0 MHz. In some embodiments, the ultrasound energy may have a frequency of about 20 KHZ, about 50 kHZ, about 100 kHZ, about 150 kHZ, about 200 kHZ, about 250 kHZ, about 300 kHZ, about 400 kHZ, about 500 kHZ, about 600 kHZ, about 700 kHZ, about 800 kHZ, about 900 kHZ, or about 1000 KHz. In some embodiments, the ultrasound energy may have a frequency of about 1.0 MHz, about 1.5 MHz, about 2.0 MHz, about 2.5 MHz, about 3.0 MHz, about 4 MHz, about 5.0 MHz, about 6.0 MHz, about 7.0 MHz, about 8.0 MHz, about 9.0 MHz, or about 10.0 MHz. In some embodiments, the ultrasound energy may have a frequency of between about 0.02 and about 0.05 MHz, between about 0.05 and about 0.25 MHz, between about 0.10 and about 0.80 MHz between about 0.5 and about 1.0 MHz, between about 1.0 and about 5.0 MHz, between about 2.5 and about 7.5 MHz, or between about 1.0 and about 10.0 MHz.

In some embodiments, the ultrasound energy may have an amplitude in a range of about 0.01 mm to about 1.0 mm. In some embodiments, the ultrasound energy may have an amplitude of about 0.01 mm, about 0.05 mm, about 0.08 mm, about 0.10 mm, about 0.25 mm, about 0.5 mm, about 0.75 mm, or about 1.0 mm. In some embodiments, the ultrasound energy may have an amplitude of between about 0.01 and about 0.10 mm, between about 0.05 and about 0.25 mm, between about 0.15 and about 0.45 mm, between about 0.25 and about 0.75 mm, between about 0.30 and about 0.90 mm, or between about 0.10 and about 1.0 mm.

In some embodiments, the duration of application or exposure of the ultrasound energy ranges from about 30 seconds to about 60 minutes. In some embodiments, the duration of exposure of ultrasound energy is about 30 seconds. In some embodiments, the duration of exposure of ultrasound energy is about 1 minute. In some embodiments, the duration of exposure of ultrasound energy is about 5 minutes. In some embodiments, the duration of exposure of ultrasound energy is about 8 minutes. In some embodiments, the duration of exposure of ultrasound energy is about 10 minutes. In some embodiments, the duration of exposure of ultrasound energy is about 15 minutes. In some embodiments, the duration of exposure of ultrasound energy is about 30 minutes. In some embodiments, the duration of exposure of ultrasound energy is about 45 minutes. In some embodiments, the duration of exposure of ultrasound energy is about 60 minutes. In some embodiments, the duration of exposure of ultrasound energy is between about 1 and about 5, between 5 and about 15, between about 10 and about 30, between about 15 and about 45, or between about 30 and about 60 minutes.

In some embodiments, the RF energy and/or ultrasound energy is applied to sinus cavities near the skin surface. In some embodiments, the RF energy and/or ultrasound energy is applied to sinus cavities at a depth below the skin surface. In some embodiments, the RF energy and/or ultrasound energy is applied about between about 1 to about 2 cm below the surface. In some embodiments, the RF energy and/or ultrasound energy is applied about between about 1 to about 5 cm below the surface. In some embodiments, the RF energy and/or ultrasound energy is applied about between about 0.5 to about 3.5 cm below the surface. In some embodiments, the RF energy and/or ultrasound energy is applied about between about 1 cm below the surface. In some embodiments, the RF energy and/or ultrasound energy is applied about between about 2 cm below the surface. In some embodiments, the RF energy and/or ultrasound energy is applied about between about 3 cm below the surface. In some embodiments, the RF energy and/or ultrasound energy is applied about between about 4 cm below the surface. In some embodiments, the RF energy and/or ultrasound energy is applied about between about 5 cm below the surface.

As described herein, RF energy generates heat via resistive interactions with mucus and tissue, while ultrasound energy converts mechanical vibrations into thermal energy through absorption. By raising the temperature of the mucus to a therapeutic range, the applied energy disrupts intermolecular bonds within the mucus, reducing its viscosity and elasticity. This thermal effect facilitates mucus mobilization and clearance, improving respiratory function and reducing congestion while minimizing discomfort.

In some embodiments, application of the RF energy and/or ultrasound energy increases the temperature of the mucus to a range sufficient to reduce its viscosity and elasticity. In some embodiments, the temperature is between about 98.0° F. and about 112.0° F. In some embodiments, the temperature of the mucus is raised to about 98.0° F. In some embodiments, the temperature of the mucus is raised to about 99.0° F. In some embodiments, the temperature of the mucus is raised to 100.0° F. In some embodiments, the temperature of the mucus is raised to 101.0° F. In some embodiments, the temperature of the mucus is raised to 102.0° F. In some embodiments, the temperature of the mucus is raised to 103.0° F. In some embodiments, the temperature of the mucus is raised to 104.0° F. In some embodiments, the temperature of the mucus is raised to 105.0° F. In some embodiments, the temperature of the mucus is raised to 106.0° F. In some embodiments, the temperature of the mucus is raised to 107.0° F. In some embodiments, the temperature of the mucus is raised to 108.0° F. In some embodiments, the temperature of the mucus is raised to 109.0° F. In some embodiments, the temperature of the mucus is raised to 110.0° F. In some embodiments, the temperature of the mucus is raised to 111.0° F. In some embodiments, the temperature of the mucus is raised to 112.0° F.

In some embodiments, application of the RF energy and/or ultrasound energy reduces the binding interaction between bound water and mucins, the primary glycoprotein component of mucus, facilitating mucus clearance. Mucins form a gel-like network that traps water, contributing to the velocity and elasticity of mucus. By increasing the temperature of the mucus through the targeted energy application described herein, the secondary and tertiary structures of mucins may be disrupted, weakening their ability to retain water and reducing overall cohesion of the mucus matrix. In some embodiments, the mucus is thick mucus.

In some embodiments, RF and ultrasound diathermy are used in combination. In some embodiments, the combination of RF and ultrasound diathermy may provide complementary benefits and may target both superficial and deeper mucus layers to maximize therapeutic effectiveness, and maintain a more preferable safety profile. In some embodiments, the duration of exposure of the RF energy and the ultrasound energy are the same. In some embodiments, the duration of exposure of the RF energy and the ultrasound energy are not the same. In some embodiments, the RF energy is applied for a longer duration than the ultrasound energy. In some embodiments, the ultrasound energy is applied for a longer duration than the RF energy.

In some embodiments, the specific design parameters improve energy delivery into the heavy mucus, sufficient to lower viscosity and promote flow while avoiding excess, and potentially damaging, heat of surrounding tissue. In some embodiments, the range of frequencies and power levels are customized to this application along with the transducer or applicator which is sized and dimensioned appropriate to the anatomical requirement.

In some embodiments, application of RF energy and/or ultrasound energy decreases mucus viscosity relative to its baseline viscosity. In some embodiments, application of RF energy and/or ultrasound energy decreases mucus viscosity by about 10 percent to about 50 percent compared to its baseline viscosity. In some embodiments, application of RF energy and/or ultrasound energy decreases mucus viscosity by about 1 percent, about 5 percent, about 10 percent, about 15 percent, about 20 percent, about 25 percent, about 30 percent, about 35 percent, about 40 percent, about 45 percent, or about 50 percent compared to its baseline viscosity. In some embodiments, application of RF energy and/or ultrasound energy decreases mucus viscosity by between about 5 percent and about 25 percent, between about 10 percent and about 30 percent, between about 15 percent and about 45 percent, or between about 25 percent and about 50 percent compared to its baseline viscosity.

It is understood that the sinus cavities, located in the head, are typically about 1 cm to about 3 cm from the skin surface. It is further understood that the lungs, located in the chest, are typically about 5 cm to about 10 cm from the skin surface. As described above, penetration depth of diathermies, including RF energy and/or ultrasound energy, may depend on frequency, wherein lower frequencies penetrate deeper, while higher frequencies are more superficial (that is, closer to the surface).

In one embodiment, the present invention is designed to target the sinus cavities. In such an embodiment, the RF energy may be applied at frequencies between about 700 MHz and about 1 GHz, between about 750 MHz and about 950 MHz, between about 850 MHz and about 930 MHz, or between about 900 MHz and about 920 MHz, or at a specific frequency of about 915 MHz. In such an embodiment, ultrasound energy may be applied at frequencies between about 1 MHz and about 5 MHz, between about 1.5 MHz and about 4.5 MHz, between about 2 MHz and about 4 MHz, or at a specific frequency of about 3 MHz. In some embodiments, both ultrasound energy and RF energy may be applied, or only one (for example, only RF energy, or only ultrasound energy) may be applied.

In another embodiment, the present invention is designed to target the lungs. In such an embodiment, RF energy such as shortwave diathermy and/or microwave diathermy may be applied to maximize therapeutic impact. In such an embodiment, the RF energy may be applied at frequences between about 10 MHz and about 40 MHz, between about 15 MHz and about 35 MHz, or between about 25 MHz and about 50 MHz, or at a specific frequency of about 27.12 MHz, and/or about 13.56 MHz. In such an embodiment, ultrasound energy may be applied at frequences between about 0.5 MHz and 3.5 MHz, between about 0.75 MHz and about 1.75 MHZ, or at a specific frequency of about 1 MHz. In some embodiments, both ultrasound energy and RF energy may be applied, or only one (for example, only RF energy, or only ultrasound energy) may be applied.

FIG. 1 shows an embodiment of the device 100, comprising an A/C power adaptor 102, an electrical instrument to convert A/C power into an electrical signal 104, an electrical cable 106, and a transducer or applicator ("transducer/applicator") 108. In some embodiments, the electrical instrument 104 converts A/C power into electrical signals which drive either a high-frequency vibrational signal in the transducer/applicator 108 or RF energy signals in the transducer/applicator 108, or both. In some embodiments, the device comprises an electrical cable 106 which may connect the electrical instrument 104 to the transducer/applicator 108. In some embodiments, the transducer/applicator 108 provides the RF or ultrasound energy signals which may penetrate human tissue. In some embodiments, the energy signals may excite molecules in the targeted cavity, for example, in the respiratory system.

In some embodiments, the invention comprises a device for the treatment of congestion. In some embodiments, the device comprises a) an RF energy and/or ultrasound energy generator configured to operate at a frequency range of about 10 MHz to about 300 GHz for RF energy and/or about 20.0 kHz to about 10.0 MHz for ultrasound energy; b) at least one applicator configured to deliver said RF and/or ultrasound energy to mucus at an energy level sufficient to raise the temperature of the mucus to between about 98.0° F. and about 112.0° F.; c) a control unit configured to (i) monitor temperature changes in real-time to ensure safety; and (ii) modulate the frequency, power level, and duration of energy delivery; and d) a feedback system to adjust parameters based on user-specific mucus properties. In some embodiments, the control unit includes pre-programmed treatment protocols based on mucus viscosity.

In some embodiments, the RF energy and/or ultrasound energy generator is capable of pulsed delivery to minimize risks associated with continuous heating. In some embodiments, the device further comprises a temperature-controlled mechanism. In some embodiments, the mechanism limits heating to a maximum of about 120.0° F. In some embodiments, the mechanism limits heating to about 113.0° F., about 114.0° F., about 115.0° F., about 116.0° F., about 117.0° F., about 118.0° F., about 119.0° F., about 120.0° F., about 121.0° F., or about 122.0° F.

In some embodiments, the device may comprise an RF energy generator. In some embodiments, the device may comprise an ultrasound energy generator. In some embodiments, the device may comprise both an RF energy generator and an ultrasound energy generator.

Figure 5A:
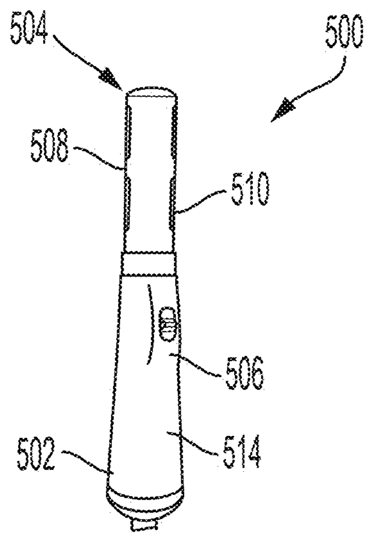
FIGS. 5A-C illustrate an embodiment of the device.
Figure 5B:
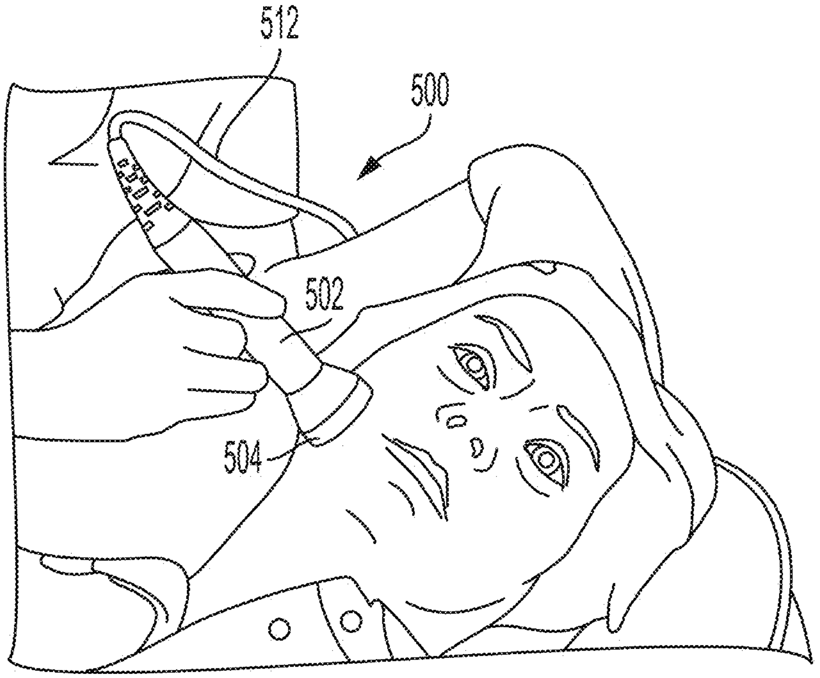
Figure 5C:
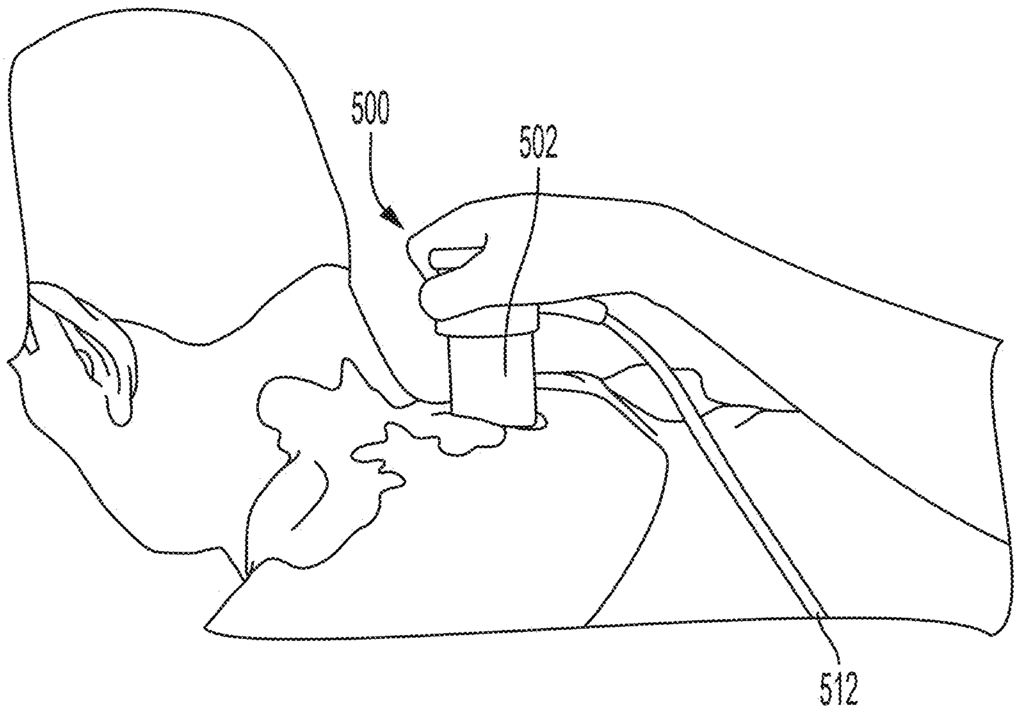

In some embodiments, and as shown in FIGS. 5A-C, the device may be a wand or hand-held apparatus 500. In some embodiments, the device may comprise an applicator 502, optionally including an applicator tip 504 for more directed application. In such an embodiment, the applicator of the device may be configured for use on the sinus region and includes an ergonomic design to conform to facial contours. In some embodiments, the device may be inserted into the mouth of the patient. In some embodiments, the device may be inserted into the nose of the patient. In some embodiments, the device may comprise an off/off switch 506. In some embodiments, the device may comprise an RF energy generator 508. In some embodiments, the device may comprise an ultrasound energy generator 510. In some embodiments, the device may comprise both an RF energy generator 508 and an ultrasound energy generator 510. In some embodiments, the device may be wireless. In some embodiments, the device may include a cord 512 to provide power or data. In some embodiments, the device may comprise a control unit 514 capable of receiving data. In some embodiments, the control unit 514 may receive data wirelessly. In some embodiments, the control unit 514 may receive data via the cord 512.

Figure 6A:
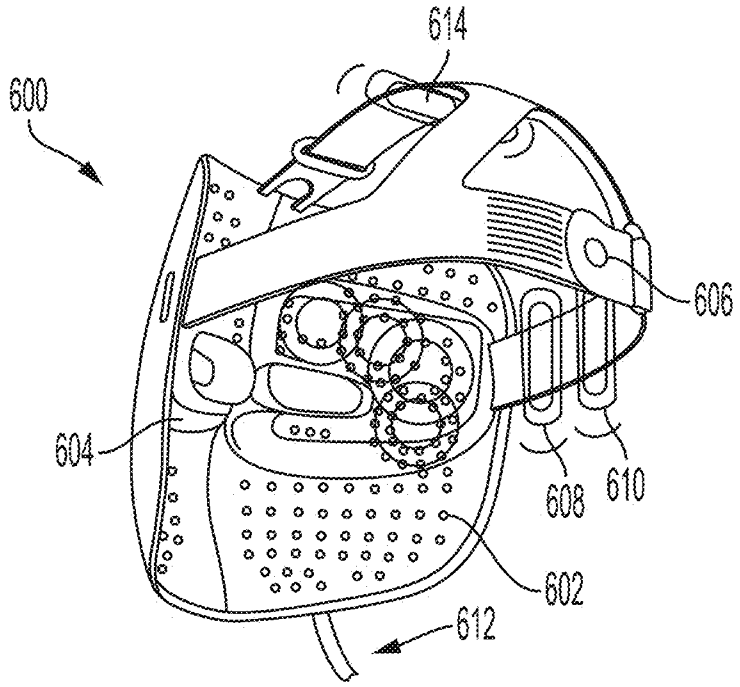
FIGS. 6A-B illustrate an embodiment of the device.
Figure 6B:
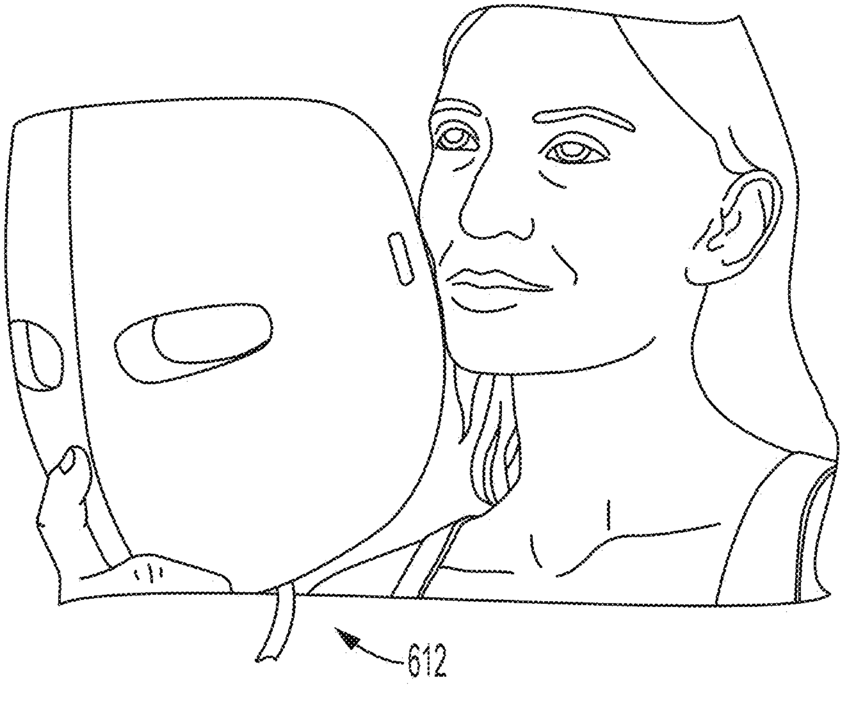

In some embodiments, as shown in FIG. 6A-B, the device may be a mask or wearable apparatus 600 which affixes to the head or the face of a user. In some embodiments, the device may comprise an applicator surface 602. In such an embodiment, the applicator of the device may be configured for use on the sinus region and includes an ergonomic design to conform to facial contours. In some embodiments, the device may comprise one or more pads 604 to provide facial comfort. In some embodiments, the device may comprise an off/off switch 606. In some embodiments, the device may comprise an RF energy generator 608. In some embodiments, the device may comprise an ultrasound energy generator 610. In some embodiments, the device may comprise both an RF energy generator 608 and an ultrasound energy 610. In some embodiments, the device may be wireless. In some embodiments, the device may include a cord to provide power or data. In some embodiments, the device may comprise a control unit 614 capable of receiving data. In some embodiments, the control unit 614 may receive data wirelessly. In some embodiments, the control unit 614 may receive data via the cord 612.

Figure 7:
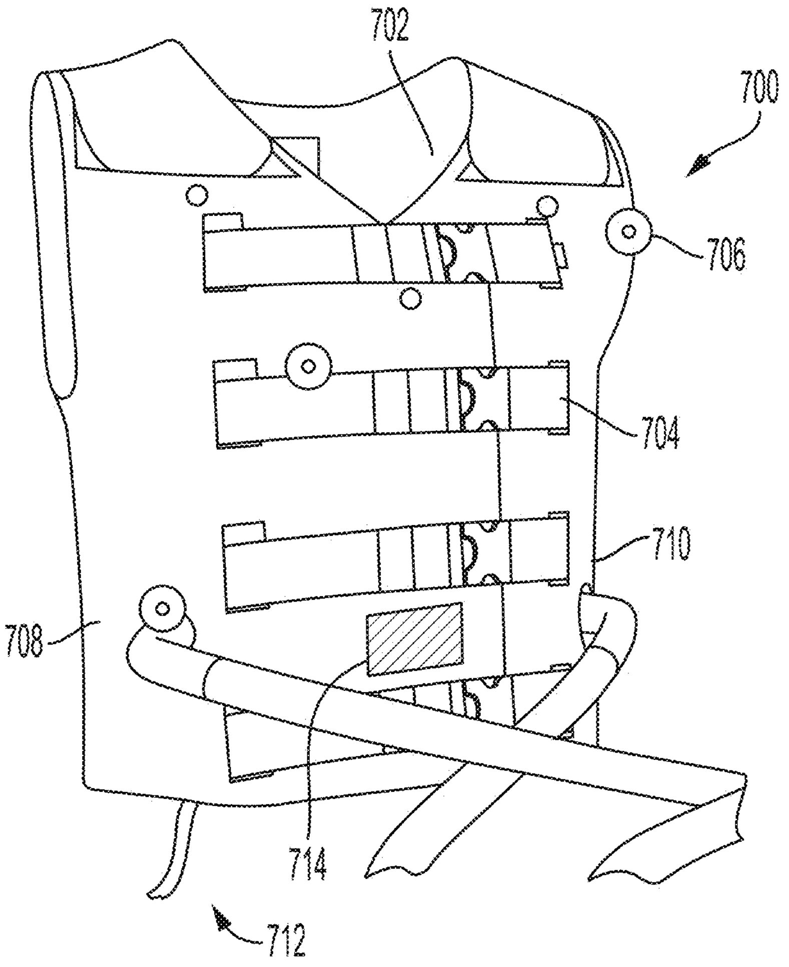
FIG. 7 illustrates an embodiment of the device, wherein the device is a vest.

In some embodiments, as shown in FIG. 7, the device may be a vest or wearable apparatus 700 which affixes to the chest, shoulders, or back of a user. In some embodiments, the device may be applied so as to align with one or more parts of the respiratory system of the patient; for example, applied to the upper middle of the back to align with the lungs. In some embodiments, the device may comprise an internal applicator surface 702. In such an embodiment, the applicator 7020 of the device may be configured for use on the chest, neck, back, or other surface and may include an ergonomic design to conform to bodily contours. In some embodiments, the device may comprise one or more latches or straps 704 to provide adjustability and comfort. In some embodiments, the device may comprise an off/off switch 706. In some embodiments, the device may comprise an RF energy generator 708. In some embodiments, the device may comprise an ultrasound energy generator 710. In some embodiments, the device may comprise both an RF energy generator 708 and an ultrasound energy 710. In some embodiments, the device may be wireless and contain an internal (wearable) battery. In some embodiments, the device may include a cord to provide power or data. In some embodiments, the device may comprise a control unit 714 capable of receiving data. In some embodiments, the control unit 714 may receive data wirelessly. In some embodiments, the control unit 714 may receive data via the cord 712.

Figure 9:
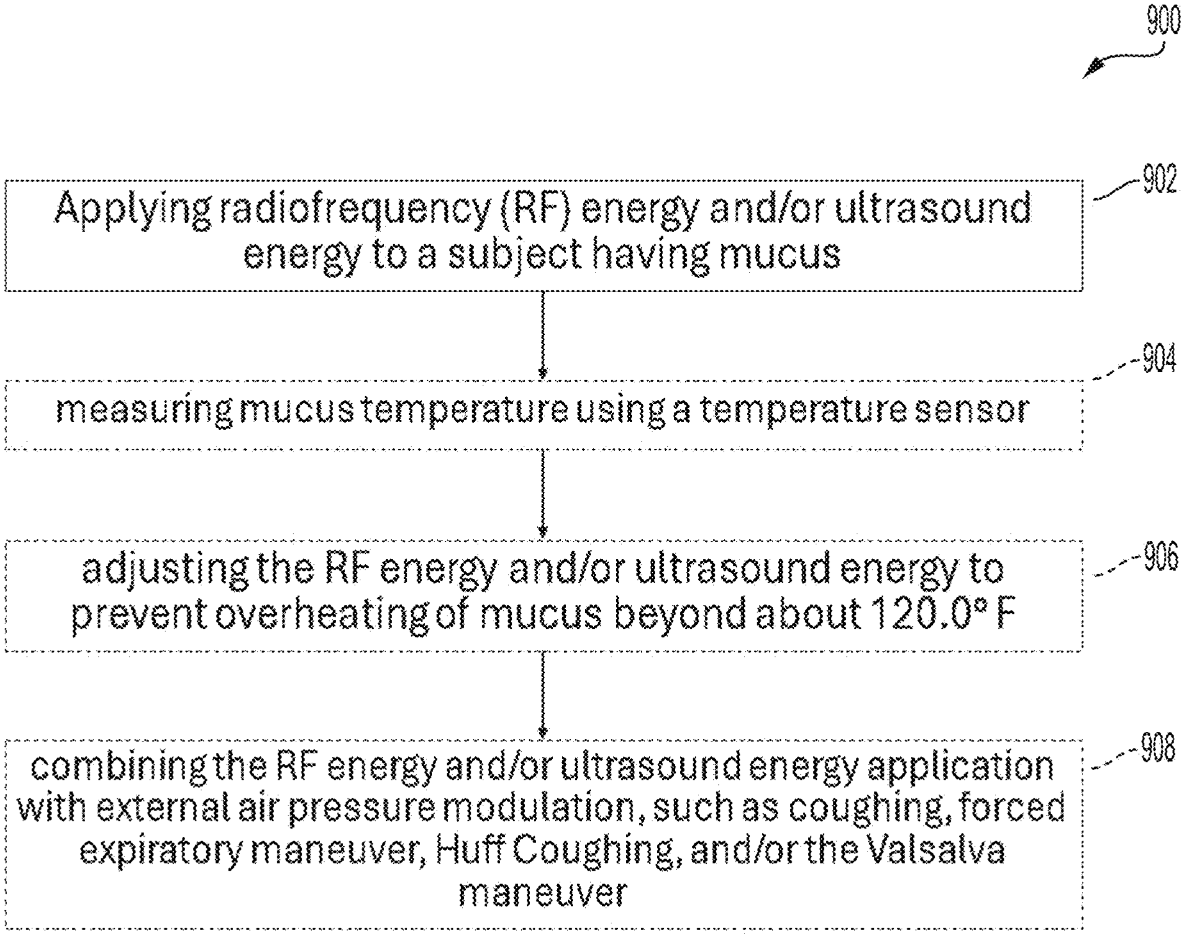
FIG. 9 is a flow chart illustrating a process according to some aspects of the invention.

In some embodiments, and as shown in FIG. 9, the invention comprises a method for treating congestion 900 as described above. In some embodiments, the method may comprise applying radiofrequency (RF) energy and/or ultrasound energy to a subject having mucus 902; wherein the RF energy and/or ultrasound energy increases the temperature of the mucus to a range sufficient to reduce its viscosity and elasticity; wherein the temperature is between about 98.0° F. and about 112.0° F. In some embodiments, the method may comprise measuring mucus temperature using a temperature sensor 904. In some embodiments, the method may comprise adjusting the RF energy and/or ultrasound energy to prevent overheating of mucus 906. In some embodiments, the maximum temperature of the mucus may be about 120.0° F. In some embodiments, the maximum temperature of the mucus may be about 113.0° F., about 114.0° F., about 115.0° F., about 116.0° F., about 117.0° F., about 118.0° F., about 119.0° F., about 120.0° F., about 121.0° F., or about 122.0° F.

In some embodiments, the method further comprises the step of combining the RF energy and/or ultrasound energy application with external air pressure modulation, such as coughing, forced expiratory maneuver, Huff Coughing, and/or the Valsalva maneuver 908.

As used herein, "mucins" refers to glycoproteins in mucus that contribute to its gel-like consistency through hydrophilic interactions, including hydrogen bonds, with water molecules. Mucin molecules can form crosslinks with each other through various interactions, such as disulfide bonds and hydrogen bonds. These crosslinks create a network structure within the mucus, giving it elasticity while still allowing it to stretch and deform. Mucus exhibits shear-thinning behavior, meaning its viscosity decreases under shear stress. When subjected to force or movement, such as during breathing or coughing, mucus becomes less viscous and flows more easily. This property allows mucus to stretch and deform without breaking, contributing to its elasticity. More specifically, mucus exhibits complex rheological properties, behaving as a thixotropic yield stress material. Yield stress materials display a dual response to applied stress: below a critical stress level, they behave like a solid, deforming elastically, while above this critical point, they shear and flow as a liquid. This critical stress is known as the yield stress. Furthermore, the thixotropic nature of mucus means its rheological properties are time-dependent and influenced by its shear history.

In some embodiments, the methods and devices described herein may be augmented by external air pressure modulation techniques to further promote mucus clearance. In some embodiments, these techniques include, but are not limited to, coughing, forced expiratory maneuvers, Huff Coughing, and the Valsalva maneuver. Such techniques may work synergistically with the energy-based methods by providing mechanical forces that complement the above-described heating and/or vibrational effects, enhancing overall mucus mobilization.

"Normal" or "thin" human mucus is understood to have a viscosity in the range of about 1,000 to about 3,000 cP at room temperature (approximately 72° F.) and the range of about 800 to about 2,500 cP at 98° F. "Thick" human mucus is understood to have a viscosity in the range of about 5,000 to about 10,000 cP at room temperature, and in the range of about 4,000 to about 8,000 cP at 98° F.

As used herein, "RF energy" or "radio waves" refers to electromagnetic waves in the radiofrequency range, capable of inducing dielectric heating to increase localized temperature, such as tissue temperature and/or mucus temperature. When RF energy is absorbed by a material, it may cause the molecules in that material to vibrate, which in turn generates heat. If the material contains molecules that participate in hydrogen bonding, the increase in temperature can weaken these bonds indirectly by providing additional thermal energy to the system. This weakening of hydrogen bonds can lead to changes in the properties or structure of the material, as described herein.

As used herein, "viscosity reduction" refers to a decrease in the resistance of mucus to flow, as measured in centipoise (cP).

As used herein, "yield stress" refers to the minimum stress required to initiate flow within mucus. Specifically, yield stress refers to the minimum stress required to transition mucus from a semi-solid ("gel-like") state to a fluid or "fluid-like" state. Yield stress quantifies the resistance of mucus to deformation under applied forces.

As used herein, "target temperature" refers to the temperature range necessary to achieve therapeutic effects. For example, as described herein, the target temperature to achieve therapeutic effects on mucus properties may be between about 98.6° F. and about 115.0° F.

As used herein, the terms "approximately" and "about," as applied to one or more values of interest, refer to a value that is +/−10% of the recited value.

The embodiments of the invention described above are intended to be merely exemplary; numerous variations and modifications will be apparent to those skilled in the art. All such variations and modifications are intended to be within the scope of the present invention as defined in any appended claims.

EXAMPLES

The following examples are intended to exemplify the present disclosures and are not limitations of the claimed invention. All molecules, compositions, methods, assays, and results disclosed in the examples form part of the present invention.

Example 1: Dependence of Human Mucus Fluidity on Temperature Variations

The dependence of human mucus fluidity on temperature variations was investigated to support an innovative approach to enhance the removal of mucus from nasal passages by enhancing its fluidity and flowability through temperature changes. Mucus is a "yield stress" fluid and demonstrates a dual response to an applied stress; that is, below a critical stress, mucus may behave like a solid, and above a critical stress, mucus may flow like a liquid. The viscosity of mucus above a yielding point dictates the degree of resistance against flow. Thus, both parameters yield stress and viscosity are important to understand the flowability of mucus samples.

To analyze the effect of temperature on the flowability of mucus, changes in yield stress were measured at two temperatures: 98° F. (37° C.) and 110° F. (43° C.). The inherently complex and viscous structure of mucus, combined with its significant yield stress and elastic response, posed challenges for accurate measurement. Additionally, the limited volume of the samples (1-2 ml) necessitated the use of specialized geometry. Roughened parallel plate geometries were utilized with a diameter of 25 mm to measure the yield stress, viscosity and flow curves (see FIGS. 2A-B). Wall-slip is a common issue in rheological measurements of gels and may result in underestimation of yield stress and viscosity. To mitigate wall-slip effects, roughened geometries were used.

The rheological measurements were carried out using the following methodologies: prior to each test, the samples were pre-sheared at a high shear rate and then remained at rest for 1 minute. The pre-shearing procedure eliminated the shear history of the material. Yield stress was determined through a stress ramp-up test, during which shear stress was increased linearly from a low value. Initially, the material exhibited non-linear elastic behavior, characterized by finite deformation in response to the applied stress. This non-linear elastic behavior led to an increase in instantaneous viscosity (measured as t/y) with increasing stress. As the stress surpassed the yield point, the material transitioned to a shear-thinning fluid, where instantaneous viscosity decreased with further increases in shear stress. The peak viscosity observed during this transition indicated the yield stress, defined as the stress at which the viscosity reached its maximum.

Figure 2A:
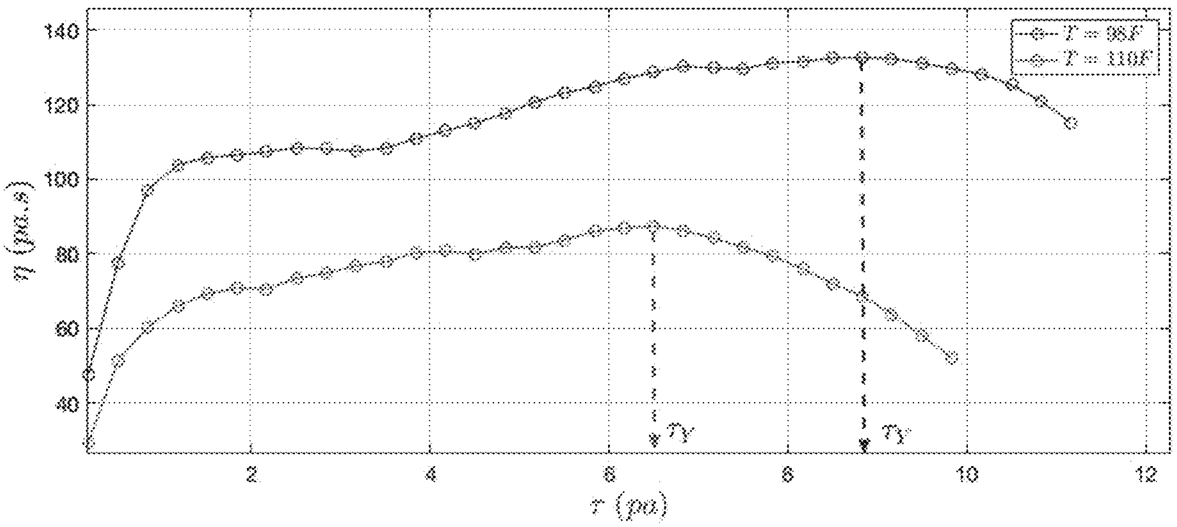
FIGS. 2A-B illustrate the results of stress ramp test for mucus Sample A (FIG. 2A) and mucus Sample B (FIG. 2B) at two different temperatures (98° F. (blue line)) and 110° F. (bottom line)). The curves represent viscosity versus shear stress. The peaks in the viscosity curves mark the yield stress. Critical stress at which viscosity drops significantly is shown in FIGS. 2A-B with dotted lines.
Figure 2B:
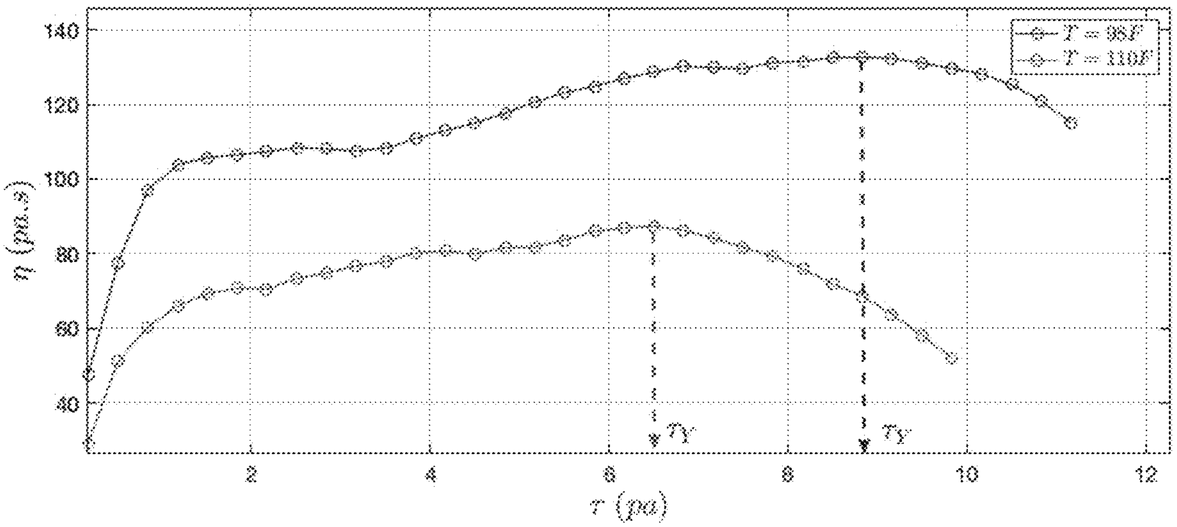

As shown in FIGS. 2A-B, the flow curve was determined using a shear rate-controlled test, in which the shear rate was decreased in a stepwise manner. At each shear rate, measurements were taken until the shear stress reached equilibrium, and the steady-state shear stress was recorded. The test parameters are detailed in Table 1.

TABLE 1

| Yield Stress and Viscosity Measurements | |
|---|---|
| Geometry | PU25 |
| Gap (H) | 1 mm |
| Environmental Controller | Peltier-Cylinder Cartridge (−30° C. to 200° C.) |
| Temperature | 98° F., 110° F. |
| Stress Ramp | 0.1-12 Pa |

To benchmark the measurements, tests were performed with a standard oil (RT100) and a sample of hair gel (data not shown). The viscosity of standard oil has been measured accurately at different temperatures and can be used as a reference to benchmark the measurements. Furthermore, hair gel, which is known as a standard yield stress material with negligible thixotropic behavior, was used to benchmark the yield stress measurement techniques and examine the repeatability of the viscosity measurement technique.

To determine the yield stress of the mucus samples, stress-ramp tests were performed. The results are shown in FIG. 2A (for Sample A) and FIG. 2B (for Sample B), respectively. By increasing the stress, the instantaneous viscosity initially increased due to the elastic response. After a critical point, the material yields, and the instantaneous viscosity decreased due to shear-thinning effects. The peak in the instantaneous viscosity marked the yielding point, TY.

The results, as shown in FIG. 2A-B, show that the yield stress of both samples decreased with increasing temperature. Specifically, as the temperature was raised from 98° F. to 110° F., the yield stress of Sample A (FIG. 2A) decreased by approximately 25%. Similarly, the yield stress of Sample B (FIG. 2B) decreased by about 26%. This significant reduction in yield stress with a relatively small increase in temperature suggests that the mucus can be easily liquefied and made to flow by raising the temperature.

Example 2: Dependence of Human Mucus Viscosity on Temperature Variations

Figure 3A:
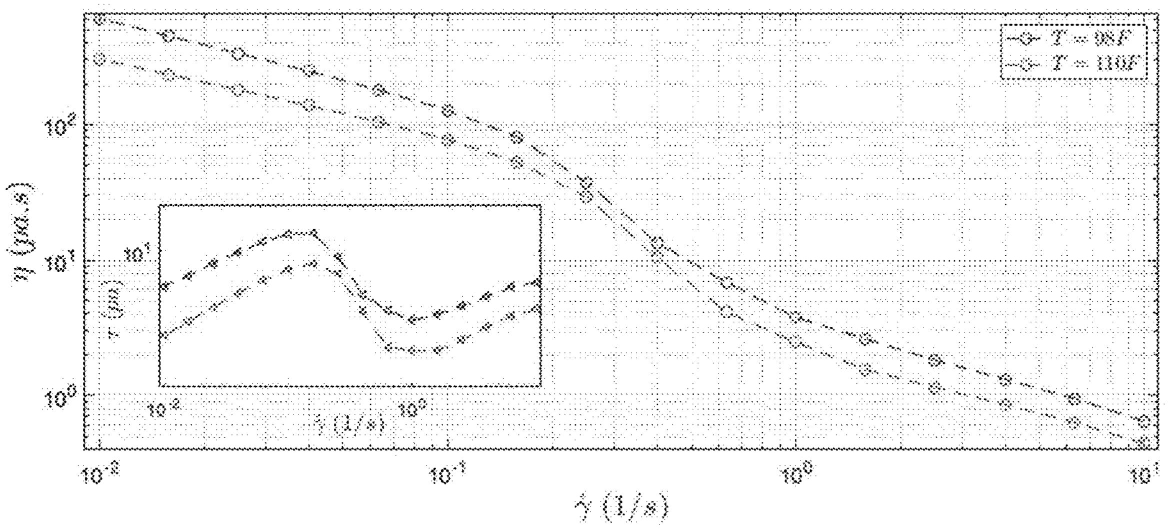
FIGS. 3A-B illustrate the flow curves for mucus Sample A (FIG. 3A) and mucus Sample B (FIG. 3B) at two different temperatures (98° F., top line and 110° F., bottom line). The curve represents steady shear viscosity versus shear rate. The inset represents the shear stress versus shear rate.
Figure 3B:
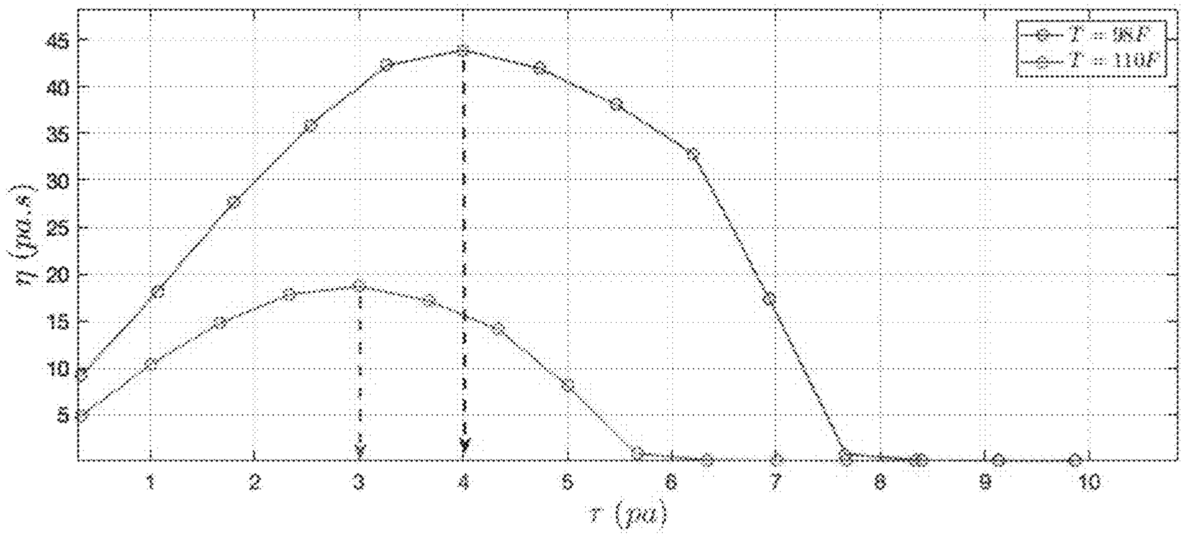

Flow curves and instantaneous viscosity measurements for Samples A and B were collected, as shown in FIGS. 3A and 3B, respectively.

As described above, and as shown in FIGS. 2A-B, the flow curve was determined using a shear rate-controlled test, in which the shear rate was decreased in a stepwise manner. At each shear rate, measurements were taken until the shear stress reached equilibrium, and the steady-state shear stress was recorded. The test parameters are detailed in Table 1.

Flow curves and viscosity measurements are crucial for understanding the flow of gels in thin conduits, illustrating how easily the material flows when subjected to a constant shear stress. The flow curves demonstrate the shear-thinning behavior of the material. As the shear rate increases, the viscosity of the material decreases. This is a common characteristic of non-Newtonian fluids, such as mucus, where the internal structure of the material breaks down under shear, leading to a reduction in viscosity.

The results of this experiment, as shown in FIGS. 3A-B, show the impact of temperature on mucus viscosity; as the temperature increased from 98° F. to 110° F., the instantaneous viscosity of the mucus decreased. This effect was more pronounced at low to medium shear rates where the mucus's internal structure remains partially intact, making the influence of temperature on viscosity more noticeable. An increase in temperature helped to liquefy a sample at lower shear stresses and facilitated faster flow under constant shear stress after the material yields. The flow curves, depicting shear stress versus shear rate, are shown in FIGS. 3A-B (FIG. 3A shows data for Sample A of human mucus; FIG. 3B shows data for Sample B of human mucus).

Also shown in FIGS. 3A-B is the presence of a "kink" at low shear rates, which indicated the shear banding behavior of the mucus. Shear banding occurred in the samples when the mucus exhibited localized regions with different shear rates under an applied stress, which led to a heterogeneous flow profile (for example, the coexistence of solid and liquid regions between parallel plates at low shear rates).

The viscosity of the mucus at three different shear rates and its change with temperature was determined, as shown in Table 2. From the data calculated, the nominal shear rate during the process of mucus removal from nasal passages was estimated. Assuming a flow rate in the range of 0.5-5 ml/min and a nasal passage diameter of roughly 2-4 mm, the nominal shear rate was estimated to be approximately 1-10 $s^{-1}$. Within this range, the viscosity of Sample A and Sample B decreased by around 33% and 16%, respectively, with a temperature increase from 98° F. to 110° F.

TABLE 2

| | | | η (pa · s) | | |
|---|---|---|---|---|---|
| | T (F) | τY (pa) | γ = 0.1/s | γ = 1/s | γ = 10/s |
| Sample A | 98° F. | 8.8 | 127.4 | 3.8 | 0.6 |
| | 110° F. | 6.5 | 77.6 | 2.4 | 0.4 |
| | Decrease % | 26% | 39% | 36% | 33% |
| Sample B | 98° F. | 4.0 | 26.3 | 1.1 | 0.19 |
| | 110° F. | 3.0 | 8.2 | 0.9 | 0.16 |
| | Decrease % | 25% | 68% | 18% | 16% |

The results described above suggest that a temperature increase of 12° F. significantly reduced the pressure required for mucus removal (by approximately 25%), demonstrating that a change in temperature can have a substantial impact on the viscosity and flowability of mucus, facilitating its removal from the nasal passages.

Example 3. Thermal Test Using 3 mm ID Tube

An experiment was conducted to evaluate the effects of increasing the temperature on the movement of thick ("heavy") mucus within a confined environment, simulating the conditions found, for example, in airways or sinus cavities.

Figure 8:
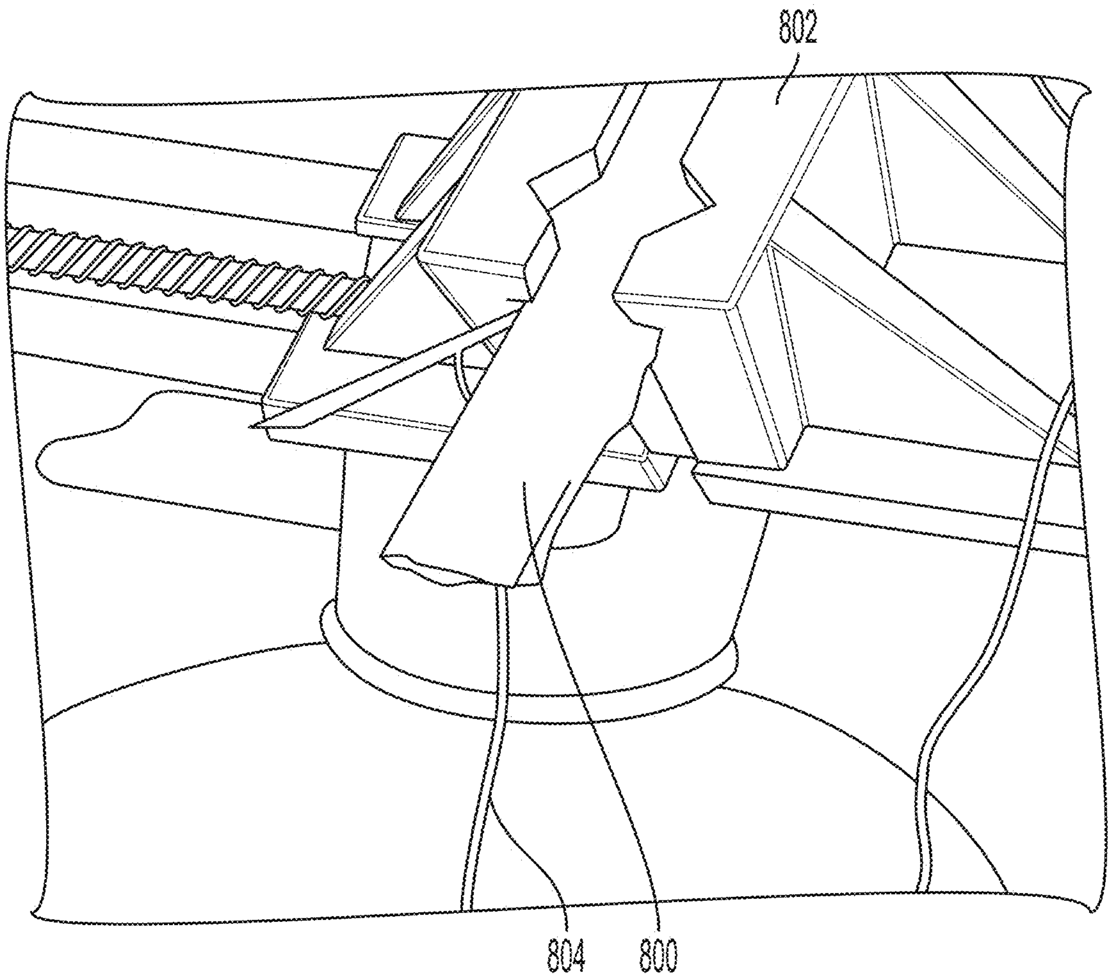
FIG. 8 illustrates a loaded silicone tube containing thick human mucus.

A flexible silicone tube with a diameter of 3 mm was selected to replicate the dimensions of small airways or sinus passages. The tube was securely clamped in place, and a resistive heating wire was wrapped evenly around the exterior of the tube to facilitate uniform heat transfer. A thermocouple temperature-sensing device 804 was inserted into the tube to monitor the internal temperature of the mucus. A sample of mucus characterized by high viscosity ("thick" or "heavy" mucus) was used to fill the tube. A schematic showing the loaded tube is shown in FIG. 8, wherein the tube 800 is held in place by a clamp 802, with an inserted thermocouple 804.

The tube was first loaded at 73° F. (ambient or room temperature) and a Eustachi device, which produces directed airflow designed to mimic natural expiratory force was employed to attempt displacement of the mucus. At 73° F., no observable effect or clearance of the mucus occurred.

The tube, filled with mucus, was placed in a standard microwave oven for a heating duration of 20 seconds. Following heating, the internal temperature of the tube was calculated to be 79° F. as measured by the thermocouple.

Following heating, the Eustachi air-blowing device was re-applied to the heated tube. The mucus was observed to fully exit the tube. The results demonstrate a significant reduction in the mucus's resistance to displacement after an increase in temperature.

Example 4. Microfluidic Testing with 2 mm Tubing

Further experiments were conducted to investigate the fluid mechanics underlying the process of mucus removal from nasal passages. The primary objective of the experiment was to determine the air pressure required to initiate mucus flow and relate it to the rheology of mucus, as influenced by temperature.

Controlled experiments were performed to examine the effect of temperature on the flowability of mucus in nasal passages. To simulate mucus flow, a microfluidic device consisting of Teflon tubing with smooth inner walls was used. The tubing was equipped with a temperature control system that included heating cables, a DC power supply, and a thermocouple. Experiments were conducted with Teflon tubing with a diameter of 2 mm. A microfluidic pressure controller (Fluigent) was used to precisely regulate air pressure at the inlet of the tubing with a resolution of 0.01 mbar.

A 9 cm section of tubing was filled with human mucus samples. The tubing was subjected to stepwise increments in inlet pressure, until the mucus began to flow. Tests were conducted at two temperatures: 98° F. and 108° F.

Figure 4A:
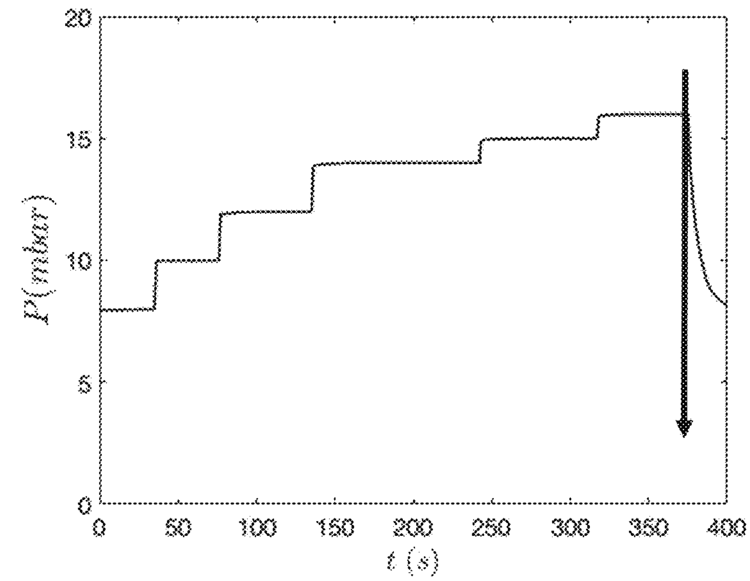
FIGS. 4A-B illustrate results for microfluidic testing of mucus at 98° F.
Figure 4B:
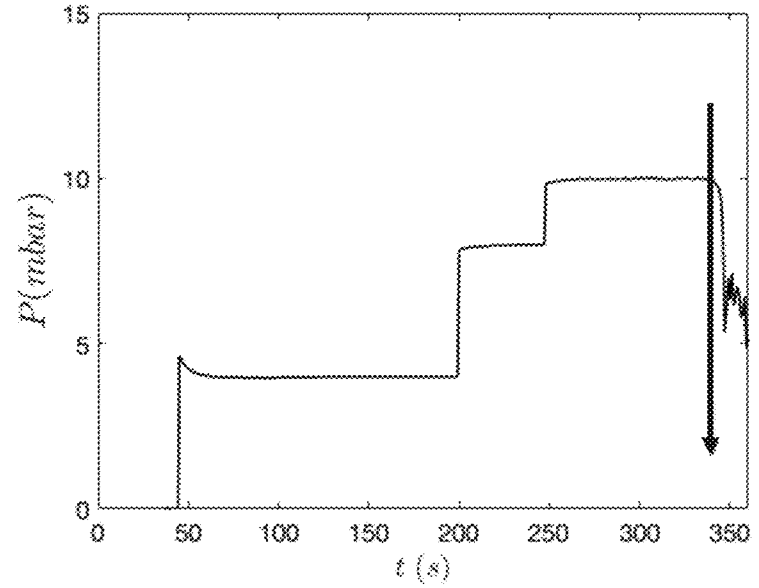

The results obtained at 98° F. and 108° F. are shown in FIGS. 4A and 4B, respectively. The results demonstrated that at 98° F., a critical pressure of approximately 16 mbar was required to initiate flow (FIG. 4A), while at 108° F., a critical pressure of approximately 10 mbar was required to initiate flow (FIG. 4B). These results indicate that an increase in the temperature of the mucus by 10° F. degrees results in a decrease in the critical pressure required for mucus removal by approximately 35%. This reduction in critical pressure aligned with the observed decrease in yield stress and viscosity at higher temperatures, as indicated by the rheological measurements (see Table 2).

OTHER EMBODIMENTS

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims. Section headings, the materials, methods, and examples are illustrative only and not intended to be limiting.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

Other aspects, advantages, and modifications are within the scope of the following claims.

What is claimed is:

1. A method for treating congestion, the method comprising:

applying ultrasound energy from a device to a subject having mucus;

wherein the device is located external to the subject and wherein no portion of the device enters a nasal cavity of the subject;

wherein the ultrasound energy is applied at:

a frequency of between about 500 kHz and about 2 MHz; and a duration of between about 5 minutes and about 60 minutes; and ceasing the application of the ultrasound energy at a time when a target temperature of the mucus is reached, wherein the target temperature is between about 100° F. and about 112° F.

2. The method of claim 1, wherein the mucus is thick mucus.

3. The method of claim 1, wherein the device is configured to reduce mucus viscosity by about 10 percent to about 50 percent compared to its baseline viscosity.

4. The method of claim 1, wherein the device is configured to emit ultrasound energy to reduce the binding interaction between bound water and mucins, facilitating mucus clearance.

5. The method of claim 1, wherein the device is configured to emit ultrasound energy to break chemical bonds which create the elasticity and stickiness of the mucus.

6. The method of claim 1, wherein the ultrasound energy is applied from the device to sinus cavities at a depth of about 1 to about 3 cm below the skin surface.

7. The method of claim 1, further comprising the step of combining the ultrasound energy application with external air pressure modulation.

8. A device for the treatment of congestion, comprising:

(a) an ultrasound energy generator configured to operate at a frequency range of about 500 kHz to about 2.0 MHz;

(b) at least one applicator configured to:

(i) externally deliver said ultrasound energy to mucus at an energy level sufficient to raise the temperature of the mucus to a target temperature, wherein the target temperature is between about 98.0° 100° F. and about 112.0° F. and (ii) provide controlled energy delivery for a duration of between about 5 minutes and about 60 minutes, wherein no portion of the device enters a nasal cavity of a subject during said delivery;

(c) a control unit configured to:

i. monitor temperature changes in real-time to ensure safety; and ii. modulate the frequency and duration of energy delivery; and iii. cease operation of the application of ultrasound energy at a time when the target temperature of the mucus is reached; and (d) a feedback system to adjust parameters based on user-specific mucus properties.

9. The device of claim 8, wherein the applicator is configured for use on the sinus region and includes an ergonomic design to conform to facial contours.

10. The device of claim 8, further comprising a temperature-controlled mechanism to limit heating to a maximum of about 112.0° F.

11. The device of claim 8, wherein the ultrasound energy generator is capable of pulsed delivery to minimize risks associated with continuous heating.

12. The device of claim 8, wherein the control unit includes pre-programmed treatment protocols based on mucus viscosity.

13. The device of claim 8, wherein the device is a wand, mask, or vest.

14. The device of claim 8, wherein the device comprises more than one applicator.

15. The device of claim 14, wherein the more than one applicators are employed simultaneously.

* * * * *